United States Patent
Brullot et al.

(10) Patent No.: US 12,123,835 B2
(45) Date of Patent: Oct. 22, 2024

(54) PREDICTION OF PHYSICAL PROPERTIES OF SUPERABSORBENT POLYMERS

(71) Applicant: BASF SE, Ludwigshafen (DE)

(72) Inventors: Ward Brullot, Antwerp (BE); Gijs Vanhoutte, Antwerp (BE); Stijn Verbert, Antwerp (BE); Filip Mees, Antwerp (BE); Maarten Vanbel, Antwerp (BE)

(73) Assignee: BASF SE, Ludwigshafen (DE)

( * ) Notice: Subject to any disclaimer, the term of this patent is extended or adjusted under 35 U.S.C. 154(b) by 575 days.

(21) Appl. No.: 17/291,692

(22) PCT Filed: Nov. 29, 2019

(86) PCT No.: PCT/EP2019/083176
§ 371 (c)(1),
(2) Date: May 6, 2021

(87) PCT Pub. No.: WO2020/109601
PCT Pub. Date: Jun. 4, 2020

(65) Prior Publication Data
US 2022/0003679 A1    Jan. 6, 2022

(30) Foreign Application Priority Data

Nov. 29, 2018  (EP) .................................... 18209220
Dec. 18, 2018  (EP) .................................... 18213570

(51) Int. Cl.
*G01N 21/65*  (2006.01)
*B01J 20/28*  (2006.01)
(Continued)

(52) U.S. Cl.
CPC ........... *G01N 21/65* (2013.01); *G01N 33/442* (2013.01); *G16C 20/30* (2019.02); *G16C 60/00* (2019.02);
(Continued)

(58) Field of Classification Search
CPC ...... G01N 21/65; G01N 33/442; G16C 20/30; G16C 60/00; B01J 20/28002;
(Continued)

(56) References Cited

U.S. PATENT DOCUMENTS 6,239,230 B1   5/2001   Eckert et al.
6,241,928 B1   6/2001   Hatsuda et al.
(Continued)

FOREIGN PATENT DOCUMENTS

DE    33 14 019 A1    1/1984
DE    35 23 617 A1    1/1986
(Continued)

OTHER PUBLICATIONS

Adar et al., Raman spectroscopy for process/quality control, Applied Spectroscopy Reviews, 32(1/02):45-101 (1997).
(Continued)

*Primary Examiner* — Mohammad K Islam
(74) *Attorney, Agent, or Firm* — Element IP, PLC

(57) ABSTRACT

The present disclosure relates to a method of predicting physical properties, in particular performance parameters, of superabsorbent polymers.

14 Claims, 10 Drawing Sheets

(51) Int. Cl.
  *G01N 33/44*  (2006.01)
  *G16C 20/30*  (2019.01)
  *G16C 60/00*  (2019.01)
(52) U.S. Cl.
  CPC ...... *B01J 20/28002* (2013.01); *B01J 2220/68* (2013.01)
(58) Field of Classification Search
  CPC ..... B01J 2220/68; G01J 3/4412; G06F 17/18; G06N 3/08
  See application file for complete search history.

(56) References Cited

U.S. PATENT DOCUMENTS

| | | | | |
|---|---|---|---|---|
| 2004/0133364 | A1* | 7/2004 | Marrow | B01J 19/2435 |
| | | | | 702/30 |
| 2004/0233425 | A1* | 11/2004 | Long | C08F 210/16 |
| | | | | 356/301 |
| 2007/0019190 | A1* | 1/2007 | Marrow | G01N 21/65 |
| | | | | 356/301 |
| 2009/0131633 | A1* | 5/2009 | Flohr | C08J 3/28 |
| | | | | 528/490 |
| 2012/0330258 | A1* | 12/2012 | Poruthoor | A61F 13/51405 |
| | | | | 493/320 |
| 2019/0067737 | A1* | 2/2019 | Zhi | H01M 4/926 |
| 2021/0085819 | A1* | 3/2021 | Brewster | A61L 15/60 |
| 2023/0116072 | A1* | 4/2023 | Herzog | G01J 3/4406 |
| | | | | 356/300 |
| 2023/0194568 | A1* | 6/2023 | Uerpmann | G01R 1/06755 |
| | | | | 324/755.01 |

FOREIGN PATENT DOCUMENTS

| | | |
|---|---|---|
| DE | 38 25 366 A1 | 2/1989 |
| DE | 195 43 368 | 5/1997 |
| DE | 196 46 484 | 5/1997 |
| DE | 102 04 938 A1 | 8/2003 |
| DE | 103 31 450 A1 | 1/2005 |
| DE | 103 31 456 A1 | 2/2005 |
| DE | 10355401 A1 | 6/2005 |
| EP | 0 083 022 A2 | 3/1988 |
| EP | 0 450 922 A2 | 10/1991 |
| EP | 0 530 438 A1 | 3/1993 |
| EP | 0 543 303 A1 | 5/1993 |
| EP | 0 547 847 A1 | 6/1993 |
| EP | 0 559 476 A1 | 7/1997 |
| EP | 0 632 068 B1 | 8/1998 |
| EP | 0 937 736 A2 | 8/1999 |
| EP | 0 640 330 B1 | 5/2000 |
| EP | 1 493 453 | 12/2010 |
| EP | 2 535 027 A1 | 8/2022 |
| JP | 2006517987 A | 8/2006 |
| JP | 2008 501 837 A | 1/2008 |
| JP | 2010504534 A | 2/2010 |
| KR | 10-2006-0024318 | 3/2006 |
| WO | WO-90/15830 | 12/1990 |
| WO | WO-93/21237 A1 | 10/1993 |
| WO | WO-0138402 A1 | 5/2001 |
| WO | WO-2002/032962 A2 | 4/2002 |
| WO | WO-03/022896 A1 | 3/2003 |
| WO | WO-03/051415 A1 | 6/2003 |
| WO | WO-2003/104299 A1 | 12/2003 |
| WO | WO-2003/104300 A1 | 12/2003 |
| WO | WO-2003/104301 A1 | 12/2003 |
| WO | WO-2005049663 A2 | 6/2005 |
| WO | WO-2005/097313 A1 | 10/2005 |
| WO | WO-2006/034806 A1 | 4/2006 |
| WO | WO-2006/034853 A1 | 4/2006 |
| WO | WO-2007/018739 A1 | 2/2007 |
| WO | WO-2009/115472 A1 | 9/2009 |
| WO | WO-2020109601 A1 | 6/2020 |

OTHER PUBLICATIONS

Milhomens et al., Biocompatibility and adsorption properties of hydrogels obtained by graft polymerization of acrylic acid on cellulose from rice hulls, Iranian Polymer Journal, 27(12):1023-32 (2018).
International Application No. PCT/EP2019/083176, International Search Report and Written Opinion, mailed Jan. 7, 2020.
F. L. Buchholz and A. T. Graham, "Modern Superabsorbent Polymer Technology" Wiley-VCH, 1998, pp. 71 to 103.
Metals Handbook, Materials Characterization, American Society for metals, first edition, Aug. 1993, p. 161, China Machine Press.
Yulin, Qiao; "Lubricating and self-preparing technology of nanoparticles", first edition, Sep. 2005, p. 141, National Defense Industry Press.

* cited by examiner

PREDICTION OF PHYSICAL PROPERTIES OF SUPERABSORBENT POLYMERS

CROSS-REFERENCE TO RELATED APPLICATIONS

This is the U.S. national phase of International Application No. PCT/EP2019/083176, filed Nov. 29, 2019, which claims the benefit of European Patent Application No. 18209220.5, filed Nov. 29, 2018, and European Patent Application No. 18213570.7, filed Dec. 18, 2018.

The present disclosure relates to a method of predicting physical properties, in particular performance parameters, of superabsorbent polymers.

Background Superabsorbent polymers (SAP) are well-known materials that commonly are used in personal care articles such as diapers. These polymers are known to absorb several times their weight of, for example, water, saline solution, urine, blood, and serous bodily fluids.

The production of water-absorbing polymer particles is described in the monograph "Modern Superabsorbent Polymer Technology", F. L. Buchholz and A. T. Graham, Wiley-VCH, 1998, pages 71 to 103.

An important requirement for the superabsorbent polymers is the ability of the hydrogel to conduct liquid (permeability) and distribute it. The permeability of the superabsorbents is reported in the form of the saline flow conductivity (SFC). Other important performance parameters include the centrifuge retention capacity (CRC), the absorption capacity under load and the absorption rate of the superabsorbent particles, reported in the amount of liquid absorbed per gram of superabsorbent per second, i.e. free swell rate (FSR); or as the time the superabsorbent needs to absorb 20 g of liquid per g of superabsorbent (T20). Typically, water-absorbing polymer particles do not have a uniform particle size, but a particle size distribution (PSD). The particle size distribution also impacts the performance of the superabsorbent polymer.

The polymer chains of the water-absorbing polymer particles are crosslinked with one another. One effect of this is that the polymer particles are water-insoluble. The properties of the water-absorbing polymer particles can be adjusted via the amount of crosslinker used. As the amount of crosslinker rises, the centrifuge retention capacity (CRC) falls and the absorption against pressure (AAP) passes through a maximum.

To improve the use properties, for example permeability and absorption under load, water-absorbing polymer particles are generally surface crosslinked. This increases the level of crosslinking of the particle surface, and in this way it is possible to at least partly decouple absorption under load and retention capacity. Crosslinkers suitable for surface crosslinking are compounds which can form covalent bonds to at least two carboxylate groups of the water-absorbing polymer particles.

The production of water-absorbing polymer particles is described, for example, in WO 01/038402 A1, WO 03/022896 A1, WO 03/051415 A1, WO 2006/034806 A1, WO 2006/034853 A1 and WO 2009/115472 A1.

WO 2005/097313 A1 discloses a process for producing water-absorbing polymer particles, in which an aqueous polymer gel is comminuted and forced through die plates by means of an extruder, dried and surface crosslinked, which gives polymer particles having a high CRC, SFC and FSR.

The measurement of the performance properties of superabsorbent polymers requires substantial analytical efforts, in particular if an industrial production process of superabsorbent polymers has to be monitored to ensure a constant quality of the product produced. It would be desirable to have a fast, simple and reliable method for determining physical properties of superabsorbent polymers involving limited measuring effort.

An objective of the present disclosure is to provide a reliable tool for predicting physical properties, in particular performance parameters, of superabsorbent polymers.

US 2004/133364 A1 discloses methods for determining and controlling properties of a polymer product, i.e., polyolefin particles, on-line in a slurry reactor system, such as a stirred slurry or slurry loop reactor. The methods include obtaining a regression model for determining a polymer product property, the regression model including principal component loadings and principal component scores, acquiring a Raman spectrum of polymer product in the slurry reactor system, calculating a new principal component score from at least a portion of the Raman spectrum and the principal component loadings, and calculating the polymer product property by applying the new principal component score to the regression model. The property can be controlled by adjusting at least one polymerization parameter based on the calculated polymer product property.

Adar, F. et al.: "Raman Spectroscopy for Process/Quality Control" in Applied Spectroscopy Reviews 32 (1997) 45-101 discloses the use of Raman spectroscopy in process control. The cross-linking of polyacrylamide gels is monitored to determine the percentage of reacted resin; and chemical properties of the gels are determined.

SUMMARY

A computer implemented method for predicting physical properties, in particular performance parameters, of superabsorbent polymers is provided. In the chemometric model of the present disclosure, spectroscopic data (typically Raman scattering spectra) are correlated with physical properties, in particular performance parameters, of superabsorbent polymers. A mathematical model based on a regression algorithm, e.g., a partial least square regression algorithm, correlates the spectroscopic data of the superabsorbent polymer and its physical properties, in particular performance parameters.

DETAILED DESCRIPTION

Figure 1:
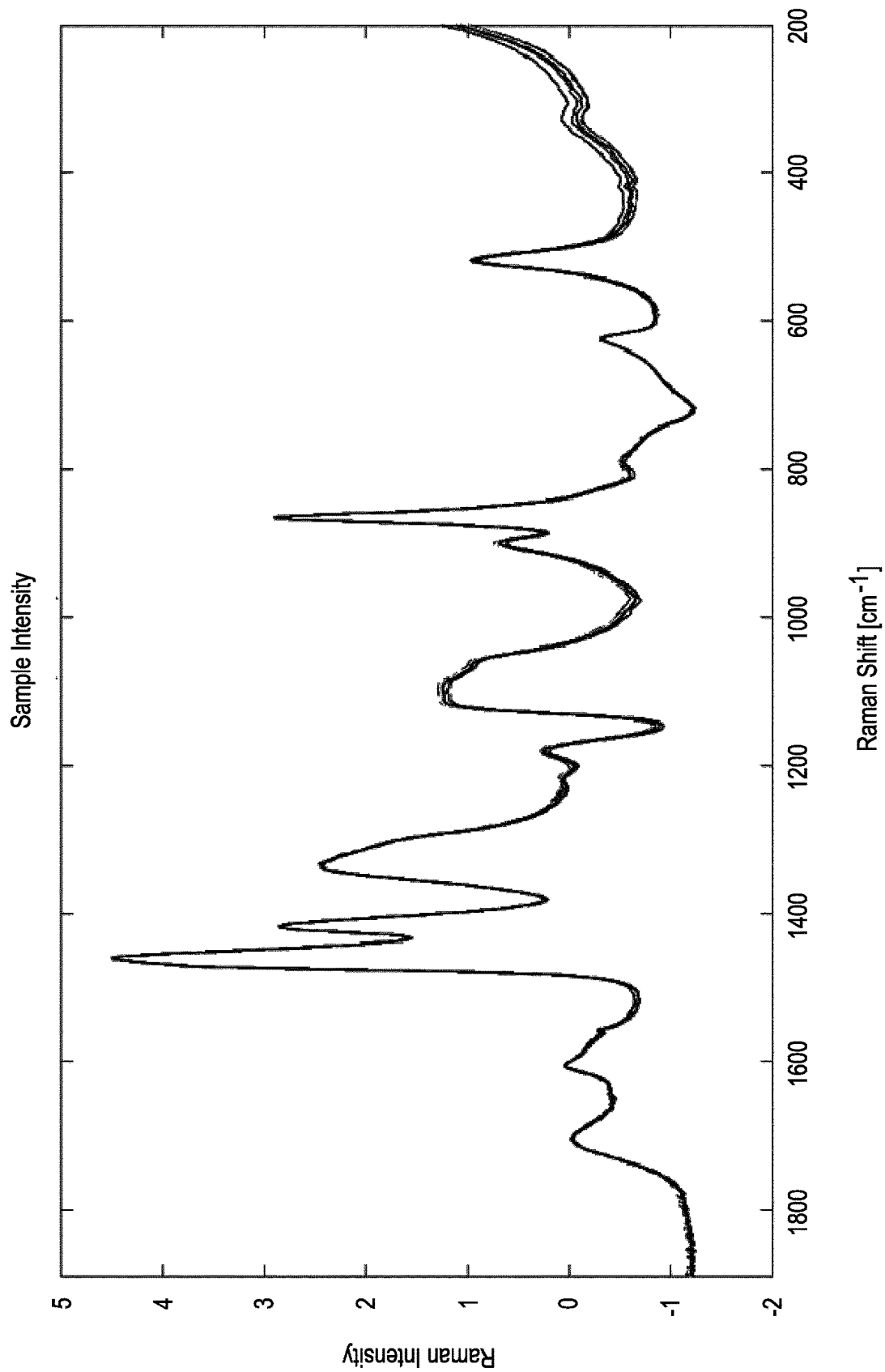
FIG. 1 shows an example of a set of 10 Raman spectra from a superabsorbent polymer with a linear fit subtraction as baseline correction and a SNV (standard normal variate) normalization step as data pre-treatment.

The present disclosure provides a method of predicting at least one physical property, particularly one performance parameter respectively, of a superabsorbent polymer (SAP), the method involving collecting a Raman spectrum of the superabsorbent polymer and using the Raman spectrum as input for a model which determines a value of the respective performance parameter from the spectroscopic data. In one embodiment, the model is based on a partial least square (PLS) regression algorithm. Other statistical modelling techniques can be used as well, for instance, ridge regression or elastic net regression. These techniques yield similar results as PLS modelling. In the present disclosure, modelling is described using PLS modelling as an example.

Fundamentally, a correlation of spectroscopic data and performance data of superabsorbent polymers is possible because the chemical composition and morphology of the superabsorbent polymers directly influence the performance parameters.

Moreover, spectroscopic analytical methods, such as Raman scattering spectroscopy, probe the chemical composition and, to a certain extent, the morphology of the polymers.

It has been found that physical properties of superabsorbent polymers, e.g., performance parameters, can be predicted using spectroscopic methods Raman spectroscopy can be used to characterize superabsorbent polymers both in an in-line and an off-line application. In one embodiment, a Raman spectrum at the fundamental wavelength of 785 nm is recorded in a timeframe between 10 seconds to 2 minutes, depending on the application.

An algorithm, a statistical factor model, is used to translate the Raman spectra into SAP physical properties, e.g., performance parameters. In one embodiment, a Partial Least-Squares or Projection to Latent Structures (PLS) model is used. Typically, a separate PLS model is used per physical property (PLS1). In an alternative embodiment, one PLS model is used for multiple properties (PLS2).

Correlating the spectroscopic data with the performance data (calibrating the model) is done using partial least square regression (PLS) modelling. This iterative algorithm determines which parts of the spectroscopic data (e.g. Raman scattering spectra) can explain the variation observed in the measured performance parameters. In the simplest model, one wavelength or wavenumber or peak in the spectroscopic data completely determines the variation in a performance parameter. However, due to the amount of different chemical groups, chain lengths, morphologies etc. present in the polymers, their weighted contributions to the performance parameters and other boundary conditions such as temperature or modus operandi of experiments, the obtained models are often complex and use large swaths of the available data to predict results.

The quality of any PLS calibration model is directly related to the quality of the data to be correlated. Spectroscopic data, such as Raman scattering spectra, are usually of high quality. In the case of superabsorbent polymers, the limiting factor is the accuracy of the measured physical properties, in particular performance parameters. It is thus important to obtain high quality data from the laboratory reference measurements by reducing or eliminating systematic errors as much as possible. Examples are reducing lab technician bias by selecting multiple persons or reducing the standard deviation of measurements by increasing the number of replicates of the same experiment on the same polymer sample.

It is also important to note that calibrated PLS models are only valid within their calibration range. As an example, if the range of CRC in the reference data is from 20-25 g/g, then the model is not suited to accurately predict CRC values outside of this range.

In one embodiment, the model has been trained with Raman spectra and measured values of the at least one physical property, in particular performance parameter, of a plurality of superabsorbent polymers covering an extended range of values of the physical property.

The first step in obtaining a model is a training phase in which (Raman scattering) spectra and measured performance parameters of several reference superabsorber samples are correlated to obtain a 'calibrated' model that can predict the performance parameters of the samples with a certain accuracy based on Raman spectra. The choice of samples (in terms of statistical distribution over parameters, number, etc.) and other settings during calibration (number of iterations, complexity of model, data pre-treatment, etc.) yield different calibration models with different characteristics in terms of robustness, accuracy and error on cross-validation.

The selection of the training samples for this first step is crucial. In the case of superabsorbent polymers, two options can be considered. The first option is training a model based on process samples, the second option is training a model using synthetic samples.

For the first option, the samples should be selected with as much process variation as possible. This to extend the calibration range as broad as possible and to reduce the influence of measurement errors on a single sample on the whole of the training sample set (e.g., a combined measurement error of 0.9 g/g CRC is more difficult to model with if the calibration range is 20-25 g/g than when it is 15-30 g/g).

A second option is the use of synthetic samples, from which the physical properties, e.g., performance parameters, are manipulated in the lab or pilot installation. These manipulations can be done based on polymers from the production process, polymers from a pilot installation, or polymers from lab syntheses. Typical examples of manipulations are mixing various particle sizes (via sieve cuts) from production samples to obtain new 'artificial' particle size distributions (PSD), which lead to a broad range in performance properties. A second example of a manipulation is to use base polymers from the production installation and transform these into surface post-crosslinked superabsorbent polymers in the lab under various conditions, e.g., different surface crosslinker, a broad temperature range, a change in reaction time, etc. A third example of a manipulation is to use of the same reagents as in the production process, but to synthesize the superabsorbent polymers in a lab environment. A fourth example for obtaining a range of synthetic samples is changing process parameters in a pilot installation to extremes that are rare in a real production environment. Other methods of producing superabsorbent polymers with a broad variation in performance properties can also be used to synthesize 'synthetic' samples as training samples for the chemometric model. This second option is linked to an offline model only.

In the second step of the modelling process, the calibration models obtained in the first step are validated using independent test samples (batches that were not used in the training phase). The calibration model yielding the best results in the validation in terms of error on prediction, reduced complexity, robustness etc. is then chosen to predict the performance parameters of other samples.

To ensure robust performance of the predictive model, continuous validation is used in one embodiment of the method. This is done in silico by determining the fit of any newly measured spectrum to the spectra used to train the model and also in the laboratory by comparing the predicted results with actual measured data (with the same level of accuracy). Validation plans, including frequencies and sample points, can be designed based on the model performance (as assessed in step 2 of the modelling process) and the required specifications of the polymers. For example, more frequent validation will be required for a model that predicts a parameter with an error of prediction of 1 in a specification range of 20-25 than for a model with an error of 0.1. If it is detected that the performance of the model is not as required (for instance, if parameters are outside the calibration range), extra reference samples can be included in the model or the model can be retrained.

When a change of recipe in the production of a superabsorbent polymer occurs, the validity of an existing model for a new recipe will strongly depend on the changes made to the recipe. If the changes are limited to small deviations in ratios of already used reagents or small changes to physical parameters such as temperatures during processing and the resulting performance parameters are within the calibration range of the model, then the probability of a successful transfer to the new recipe using the existing model is high. When changing the chemistry of the products (e.g. a new reagent) or applying strong deviations in process parameters, the probability of a successful transfer is low. In both cases, the validity of the existing model needs to be verified. Two of the possible options are pre-startup validation using synthetic samples, or an intensified validation plan at startup.

In one embodiment of the training step, a plurality of Raman spectra has been collected for each superabsorbent polymer and the spectroscopic data have been pre-treated by baseline correction of each Raman spectrum, optional smoothing or generation of a derivative of each Raman spectrum, and subsequent normalization of the Raman spectra.

In one embodiment, the spectra are pre-treated on the x-axis and on the y-axis. On the former this is done by three actions: (1) resampling with a reference spectrum, to assure that the Raman shift of the model corresponds to the Raman shift of the measured spectrum; (2) defining a global range of the spectrum that is considered for the model, typically 200-1800 $cm^{-1}$; and (3) defining 'excluded' ranges, these are ranges that the model neglects, e.g. 920-1130 $cm^{-1}$, the latter being an optional optimization step depending on the product that is being characterized. Pre-treatments on the y-axis can be done by three actions: (1) baseline correction, (2) smoothing and/or derivation, and (3) normalization. Combinations of these pre-treatments are optimized depending on the product that is being characterized.

In an exemplary embodiment, the first is a baseline correction by subtracting a straight line or a linear fit from the Raman spectrum. Alternatively, a simpler baseline correction is the use of an offset subtraction or no correction at all. A more complex correction can be a rubber band subtraction.

The second y-axis pre-treatment is smoothing the spectra or the use of the derivative of the spectra (1st or 2nd order derivative). This pre-treatment step is used to optimize the signal-to-noise ratio, considering that this can result in a loss of information. Therefore, it is preferred to improve the quality of the spectra before using this pre-treatment, e.g. by recording in a longer timeframe or averaging more recordings of the same sample.

The final pre-treatment is the normalization of the spectra. In an exemplary embodiment, spectra are normalized based on the area or by standard normal variate (SNV) normalization. The former scales the signal area under the spectrum to 1. The latter scales the signal intensity to fit a standard normal distribution. This is thus a weighted normalization where not all points contribute equally to the normalization. Alternative normalization steps can be min-max normalization, where the minimum of the signal intensity is equalized to 0 and the maximum to 1 resulting in a relative intensity with a range from 0-1. Another alternative is a peak normalization, where the signal intensity is scaled with respect to a reference peak, typically a peak that is not influenced by the performance parameters.

The combination and selection of pre-treatments depends on the model and product under investigation, but typically a straight line subtraction or linear fit subtraction is combined with an area or SNV normalization, without the use of a smoothing filter or derivative.

During the modelling/training step of the PLS model, various model performance parameters or model KPIs are optimized: Root Mean Square Error of Cross Validation (RMSECV), Root Mean Square Error of Prediction (RMSEP), $R^2$, Spectral Residuals, and Mahalanobis distance. Typically, several models are made/trained and tested/validated with process samples. The best model is chosen based on the reliability, accuracy and precision of the predicted/calculated values of the product performance parameters. The validation samples are typically chosen over two independent production campaigns of the same product. Once a set of model parameters and pre-treatments is chosen, the model is evaluated by assessing (the trend of) the Mahalanobis distance and the Spectral Residuals on a continuous basis and by periodical control samples, typically one sample every week. Extra training samples can be added to the model to improve the predictive power over time, e.g. when the difference between the model predictions and the reference values exceed the user defined limit, e.g. confidence interval. Feature selection in the Raman spectra can be used to optimize model performance.

In one embodiment of the method of the present disclosure, the Raman spectrum of the superabsorbent polymer is collected in-line in a production process of the superabsorbent polymer. In another embodiment, the Raman spectrum of the superabsorbent polymer is collected off-line on a sample of the superabsorbent polymer.

In one embodiment of the method of the present disclosure, the physical property predicted is a performance parameter of the superabsorbent polymer.

Performance parameters of the superabsorbent polymer include centrifuge retention capacity (CRC), Absorbency Under Load (AUL), effective capacity (EFFC), saline flow conductivity (SFC), T20, Free Swell Rate (FSR), Fixed Height Absorption (FHA), Permeability Dependent Absorption Under Pressure (PDAUP) and Vortex. Other important physical properties of the superabsorbent polymer include flow rate, bulk density, and residual monomer content in the core structure.

In one particular embodiment, the performance parameter is the centrifuge retention capacity (CRC) of the superabsorbent polymer. The CRC measures the liquid absorbed by the superabsorbent polymer particles for swelling in excess liquid. The CRC is measured according to EDANA test method NWSP 241.0.R2 (15) (ISO 17190-6:2001)"Polyacrylate Superabsorbent Powders—Determination of the Fluid Retention Capacity in Saline Solution by Gravimetric Measurement Following Centrifugation", wherein for higher values of the centrifuge retention capacity larger tea bags have to be used.

In a further particular embodiment, the performance parameter is the Absorbency Under Load (AUL) or Absorption Against Pressure (AAP) of the superabsorbent polymer. The AUL of the superabsorbent polymer particles is determined according to EDANA test method No. NWSP 242.0.R2 (15) (ISO 17190-7:2001) "Polyacrylate Superabsorbent Powders—Gravimetric Determination of Absorption Against Pressure".

In another particular embodiment, the performance parameter is the effective capacity (EFFC) of the superabsorbent polymer. The Effective Capacity represents an average of the value of Centrifuge Retention Capacity (CRC) and of the value of Absorption Against Pressure (AAP) of the superabsorbent polymer particles. The effective capacity is calculated as EFFC=(CRC+AAP)/2.

In still another particular embodiment, the performance parameter is the saline flow conductivity (SFC) of the superabsorbent polymer. The saline flow conductivity represents the gel layer permeability of a swollen gel layer of water-absorbent polymer particles. It is determined as described in EP 0 640 330 A1 and the evaluation of the measurement is performed as described in EP 0 640 330 A1. The flow rate is recorded automatically. The apparatus described on page 19 and in FIG. 8 of EP 0 640 330 A1 is modified to the effect that the glass frit (40) is no longer used, the plunger (39) consists of the same polymer material as the cylinder (37) and now comprises 21 bores having a diameter of 9.65 mm each distributed uniformly over the entire contact surface. The saline flow conductivity (SFC) is calculated as follows:

$$SFC[cm^3 s/g] = (F_g(t=0) \times L_0)/(d \times A \times WP),$$

where $F_g(t=0)$ is the flow rate of NaCl solution in g/s, which is obtained by means of a linear regression analysis of the $F_g(t)$ data of the flow determinations by extrapolation to t=0, $L_0$ is the thickness of the gel layer in cm, d is the density of the NaCl solution in $g/cm^3$, A is the surface area of the gel layer in $cm^2$ and WP is the hydrostatic pressure over the gel layer in $dyn/cm^2$.

In a variation of the method, the saline flow conductivity (SFC 1.5) of the superabsorbent polymer is measured according to the so-called UPM method described in EP 2 535 027 A1 on pages 19-22.

In a further particular embodiment, the performance parameter is the time in which the superabsorbent polymer reaches a liquid uptake of 20 g liquid per g of superabsorbent polymer (T20). The time to reach a liquid uptake of 20 g/g (T20) is determined by the method disclosed in EP 2 535 027 A1 on pages 13 to 18 "K(t) Test Method (Dynamic Effective Permeability and Uptake Kinetics Measurement Test Method)".

In a further particular embodiment, the performance parameter is the Free Swell Rate (FSR) of the superabsorbent polymer. The Free Swell Rate indicates the rate at which a superabsorbent polymer can absorb a known amount of saline without neither stirring nor applying external pressure. The FSR is measured according to the following procedure: 1.00 g (=W1) of the dry water-absorbent polymer particles is weighed into a 25 ml glass beaker and is uniformly distributed on the base of the glass beaker. 20 ml of a 0.9% by weight sodium chloride solution are then dispensed into a second glass beaker. The content of this beaker is rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The free swell rate (FSR) is calculated as FSR [g/gs]=W2/(W1×t). When the moisture content of the hydrogel-forming polymer is more than 3% by weight, the weight W1 must be corrected for this moisture content.

In another particular embodiment, the performance parameter is the Moisture Content (MC) of the superabsorbent polymer. The MC of the superabsorbent polymer particles is determined according to EDANA test method No. NWSP 230.0.R2 (15) (ISO 17190-4:2001)) "Polyacrylate Superabsorbent Powders—Estimation of the Moisture Content as Weight Loss Upon Heating".

In still another particular embodiment, the performance parameter is the Fixed Height Absorption (FHA) of the superabsorbent polymer. The FHA represents the superabsorbent polymers absorption capacity of saline solution against a fixed hydrostatic pressure applied to the superabsorber. It can be measured using the method described in EP 1 493 453 A1 on pages 9/10.

In another particular embodiment, the performance parameter is the Permeability Dependent Absorption Under Pressure (PDAUP) of the superabsorbent polymer. The PDAUP represents the absorption capacity of the superabsorber under a constant pressure from the bottom up. Permeability determines the total amount of saline absorbed in the superabsorber. It can be measured according to EDANA test method NWSP 243.0.R2 (15) "Polyacrylate Superabsorbent Powders—Determination of the Permeability Dependent Absorption Under Pressure of Saline Solution by Gravimetric Measurement".

In another particular embodiment, the physical property is the particle size distribution (PSD) of the superabsorbent polymer. The particle size distribution of the superabsorbent polymer particles is determined in accordance with EDANA test method No. NWSP 220.0.R2 (15) (ISO 17190-3:2001)

"Polyacrylate Superabsorbent Powders—Determination of the Particle Size Distribution by Sieve Fractionation".

In still another particular embodiment, the physical property is the bulk density of the superabsorbent polymer. The bulk density is measured according to EDANA method NWSP 251.0.R2 (15) "Polyacrylate Superabsorbent Powders—Gravimetric Determination of Flow Rate and Bulk Density".

In still another particular embodiment, the performance parameter is the flow rate of the superabsorbent polymer. The flow rate of the superabsorbent polymer particles is determined according to EDANA test method No. NWSP 251.0.R2 (15) "Polyacrylate Superabsorbent Powders—Gravimetric Determination of Flow Rate and Bulk Density".

In still another particular embodiment, the physical property is the color value of the superabsorbent polymer. The color value is measured in agreement with the tristimulus method according to DIN 5033-6.

In another particular embodiment, the performance parameter is the surface tension of an aqueous extract of the superabsorbent polymer. The surface tension of the aqueous extract is measured according to the following method: 0.50 g of the superabsorbent polymer particles are weighed into a small beaker and 40 ml of a 0.9% by weight sodium chloride solution are added. The contents of the beaker are stirred with a magnetic stirrer bar at 500 rpm for 3 minutes, then left to settle for 2 minutes. Finally, the surface tension (ST) of the supernatant aqueous phase is measured with a K10-ST digital tensiometer or a comparable instrument with a platinum plate (Krüss GmbH, Hamburg, Germany). The measurement is conducted at a temperature of 23° C.

In still another particular embodiment, the performance parameter is the Vortex of the superabsorbent polymer. The Vortex is measured according to the following method: 50.0±1.0 ml of 0.9% NaCl solution are added into a 100 ml beaker. A cylindrical stirrer bar (30×6 mm) is added and the saline solution is stirred on a stir plate at 60 rpm. 2.000±0.010 g of superabsorbent polymer particles are added to the beaker as quickly as possible, starting a stop watch as the addition begins. The stopwatch is stopped when the surface of the mixture becomes "still". That means the surface has no turbulence, and while the mixture may still turn, the entire surface of particles turns as a unit. The displayed time of the stopwatch is recorded as Vortex time.

In one embodiment of the method of the present disclosure, the superabsorbent polymer comprises cross-linked polymer chains of at least partially neutralized acrylic acid monomer units. In one embodiment, the cross-linker is N-(2-hydroxyethyl)-2-oxazolidinone (HEONON).

An exemplary process for the production of the superabsorbent polymer particles is described in detail hereinafter.

The superabsorbent polymer particles may be produced by polymerizing a monomer solution or suspension, comprising
  a) at least one ethylenically unsaturated monomer which bears acid groups and may be at least partly neutralized,
  b) at least one crosslinker,
  c) at least one initiator,
drying the resulting polymer gel and grinding the dried polymer gel. Superabsorbent polymers typically are water-insoluble.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Acrylic acid typically comprises polymerization inhibitors, preferably hydroquinone monoethers, as storage stabilizers.

The monomer solution comprises preferably up to 250 ppm by weight, preferably at most 150 ppm by weight, more preferably at most 100 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetra-allyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

The amount of crosslinker b) is preferably 0.05 to 1.5% by weight, more preferably 0.1 to 1% by weight and most preferably 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. However, the reducing component used is preferably disodium 2-hydroxy-2-sulfonatoacetate or a mixture of disodium 2-hydroxy-2-sulfinatoacetate, disodium 2-hydroxy-2-sulfonatoacetate and sodium bisulfite. Such mixtures are obtainable as Brüggolite® FF6 and Brüggolite® FF7 (Brüggemann Chemicals; Heilbronn; Germany).

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

For better control of the polymerization reaction, it is optionally possible to add all known chelating agents to the monomer solution or suspension or to the raw materials thereof. Suitable chelating agents are, for example, phosphoric acid, diphosphoric acid, triphosphoric acid, polyphosphoric acid, citric acid, tartaric acid, or salts thereof.

The monomer solution or suspension is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928 A. Polymerization in a belt reactor forms a polymer gel which has to be comminuted in a further process step, for example in an extruder or kneader.

To improve the drying properties, the comminuted polymer gel obtained by means of a kneader can additionally be extruded.

The acid groups of the resulting polymer gels have typically been partially neutralized. Neutralization is preferably carried out at the monomer stage. This is typically accomplished by mixing in the neutralizing agent as a solid or preferably as an aqueous solution. The degree of neutralization is preferably from 50 to 90 mol %, more preferably from 60 to 85 mol % and most preferably from 65 to 80 mol % and particularly preferred from 65 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

The resulting polymer gel is dried. The driers are not subject to any restriction. However, the drying of the polymer gel is preferably performed with a belt drier until the residual moisture content is preferably 0.5 to 10% by weight, more preferably 1 to 7% by weight and most preferably 2 to 5% by weight, the residual moisture content being determined by EDANA test method No. WSP 230.2-05 "Mass Loss Upon Heating". In the case of a too high residual moisture content, the dried polymer gel has a too low glass transition temperature $T_g$ and can be processed further only with difficulty. In the case of a too low residual moisture content, the dried polymer gel is too brittle and, in the subsequent grinding steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Subsequently, the dried polymer gel is ground and classified. The mean particle size of the polymer particles removed as the product fraction is preferably at least 200 µm, more preferably from 250 to 600 µm and very particularly from 300 to 500 µm. The mean particle size of the product fraction may be determined by means of EDANA test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

To improve the properties, the polymer particles may subsequently be thermally surface post-crosslinked. Suitable surface post-crosslinkers are compounds which comprise groups which can form covalent bonds with at least two acid groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230 A.

Preferred surface post-crosslinkers are ethylene carbonate, ethylene glycol diglycidyl ether (Denacol®, Nagase ChemteX Corp, Tokyo, Japan), reaction products of polyamides with epichlorohydrin and mixtures of propylene glycol and 1,4-butanediol.

The amount of surface post-crosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface post-crosslinkers before, during or after the surface post-crosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counter ions are chloride, bromide, sulfate, hydrogensulfate, carbonate, hydrogencarbonate, nitrate, phosphate, hydrogenphosphate, di hydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface post-crosslinking is typically performed in such a way that a solution of the surface post-crosslinker is sprayed onto the dried polymer particles. After the spray application, the polymer particles coated with surface post-crosslinker are dried thermally, and the surface post-crosslinking reaction can take place either before or during the drying.

The spray application of a solution of the surface post-crosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface post-crosslinker solution in a fluidized bed.

The surface post-crosslinkers are typically used in the form of an aqueous solution. The penetration depth of the surface post-crosslinker into the polymer particles can be adjusted via the content of nonaqueous solvent and total amount of solvent.

The thermal surface post-crosslinking is preferably performed in contact driers, more preferably paddle driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany) and Nara Paddle Dryer (NARA Machinery Europe; Frechen; Germany). Moreover, fluidized bed driers may also be used.

The thermal surface post-crosslinking can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred surface post-crosslinking temperatures are in the range of 100 to 250° C., preferably 110 to 230° C., more preferably 120 to 210° C. and most preferably 150 to 190° C. The preferred residence time at this temperature in the reaction mixer or drier is preferably at least 10 minutes, more preferably at least 20 minutes, most preferably at least 30 minutes, and typically at most 60 minutes.

Subsequently, the surface post-crosslinked polymer particles can be classified again, excessively small and/or excessively large polymer particles being removed and recycled into the process.

To further improve the properties, the surface post-crosslinked polymer particles can be coated or remoisturized.

The remoisturizing is preferably performed at 30 to 80° C., more preferably at 35 to 70° C., most preferably at 40 to 60° C. At excessively low temperatures, the superabsorbent polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the saline flow conductivity (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200 (Evonik Industries AG, Essen, Germany), or precipitated silica, such as Sipernat® D17 (Evonik Industries AG, Essen, Germany), and surfactants, such as Span® 20 (Merck KGaA, Darmstadt, Germany).

The method of the present disclosure can also be used to obtain additional information on the chemical composition of a superabsorbent polymer, e.g. the concentration of residual acrylic acid or HEONON; solvents like 1,2-propane diol or 1,3-propane diol; or extractables.

Residual monomer (ReMo) content in superabsorbent polymer particles is determined according to EDANA test method No. WSP 210.2 (04) "Determination of the Amount of Residual Monomers in Superabsorbent Materials".

Another aspect of the present disclosure is the use of predicted values for physical properties of a superabsorbent polymer obtained by the method of the present disclosure for steering a production process of the superabsorbent polymer. Predicted values of physical properties, e.g., performance parameters, of the superabsorbent polymer which have been obtained by the method of the present disclosure can be used for steering the production process, i.e., controlling and optimizing process parameters or process steps, respectively, e.g., by varying the concentration of crosslinker in the polymerization step or by varying the concentration of surface-crosslinker or by optimization of the process steering parameters. A feedback loop is established that results in optimized product properties and ensures consistent product quality, i.e., less variation in product properties.

The present disclosure also provides a software product configured to perform the method of the present disclosure. In one embodiment, the software product is a computer program implemented in a plant for the production of a superabsorbent polymer, e.g., in a computing unit (a computer) integrated therein and/or connected thereto.

According to a further embodiment, the software product is a computer program product that when loaded into a memory of a computing device and executed by at least one processor of the computing device executes the steps of the above described computer implemented method.

The software product, i. e. the computer program product may be used with or incorporated in a computer system that may be a standalone unit or include one or more remote terminals or devices in communication with a central computer via a network such as, for example, the Internet or an intranet. As such, the computer or processor and related components described herein may be a portion of a local computer system or a remote computer or an on-line system or combinations thereof. Any database and the software product, i. e. the computer program product described herein may be stored in computer internal memory or in a non-transitory computer readable medium.

The present disclosure further provides a computer system for predicting at least one physical property of a superabsorbent polymer, the computer system comprising at least:
  an interface component configured to access and read a Raman spectrum of the superabsorbent polymer;
  a processor unit implementing a model and configured to use the Raman spectrum provided via the interface component as input for the model which determines a value of the physical property from the spectroscopic data, the model being based on a regression algorithm.

In one embodiment, the regression algorithm is a partial least square (PLS) regression algorithm. In another embodiment, the regression algorithm is based on ridge regression. In still another embodiment, the regression algorithm is an elastic net regression algorithm.

According to one embodiment, the system is configured to be coupled to a Raman spectrometer via a wired and/or wireless communication connection, and to access and read out the Raman spectrum at least partly automatically from the Raman spectrometer via the interface component. The system can be coupled to a plant for the production of a superabsorbent polymer or integrated in the respective plant.

According to a further embodiment, the system is configured to determine the value of the physical property from the spectroscopic data in-line in a production process of the superabsorbent polymer.

The system may further comprise a database which at least temporarily stores a plurality of measured Raman spectra and measured values of the at least one physical property of a plurality of superabsorbent polymers covering an extended range of values of the physical property, the system being further configured to train the model with the stored measured Raman spectra and the measured values of the at least one physical property.

The system may be further configured to update the model over and over again by iteratively training the model with newly measured Raman spectra and newly measured values of the at least one physical property of superabsorbent polymers.

The system is particularly configured to execute the above described method for predicting at least one physical property of a superabsorbent polymer.

The subject matter of the present disclosure is further described and explained in the following working examples.

EXAMPLES

Raman Method used to Characterize SAP

Both in the inline and offline application, Raman spectroscopy was used to characterize superabsorbent polymers. The off-line application was set up with a benchtop RamanRXN2™ Hybrid spectrometer (wavelength 785 nm) (Kaiser Optical Systems, Inc., Ann Arbor, MI 48103, U.S.A.). The in-line application was also set up with a RamanRXN2™ Hybrid spectrometer cooled in a dust-free cabinet and the laser and detector were connected to an insertion probe with a PhAT probe head (Kaiser Optical Systems, Inc., Ann Arbor, MI 48103, U.S.A.) trough optical fibers. Insertion probes were located at strategic locations in the production process, where product is free-flowing. A Raman spectrum at the fundamental wavelength of 785 nm was recorded in a timeframe between 10 sec to 2 minutes, depending on the application.

The detection window ranged from 150 $cm^{-1}$ to 1900 $cm^{-1}$. The window from 200 $cm^{-1}$ to 1800 $cm^{-1}$ was used for modelling.

The modeling software used was PEAXACT® (S•PACT GmbH, 52064 Aachen, Germany). Other modeling software may also be used, e.g., R, python, mathlab etc. For semi-automated data gathering in the lab and autonomous measurements in the process, a software solution specifically developed by S•PACT was used. The models are supplemented by software control of the Raman spectrometer. The Raman predicted performance of superabsorbent polymers reduces the spread on performance data, since the model is trained on more accurate data.

Due to the on-line capability of the technique, process steering is much faster and more effective. Using the on-line Raman device, the number of in-process samples is reduced, resulting in a reduction of work that has to be performed in the lab. It would be possible to link product release to the evaluation of the on-line Raman spectra, yielding additional reduction in lab work required.

Additionally, data on chemical properties of the superabsorbent polymers, e.g., on their chemical composition, can be extracted from the optical spectra, which can be used for product optimization. Automatic process steering can be achieved through integrating the Raman predictions into decision-making steps to optimize process settings.

FIG. 1 shows an example of a set of 10 Raman spectra obtained from a sample of a superabsorbent polymer, after a linear fit subtraction as baseline correction and a SNV normalization step as data pre-treatment. Each spectrum was obtained in the lab, by measuring 6 accumulations of 10 seconds each, thus 60 s in total.

Figure 2:
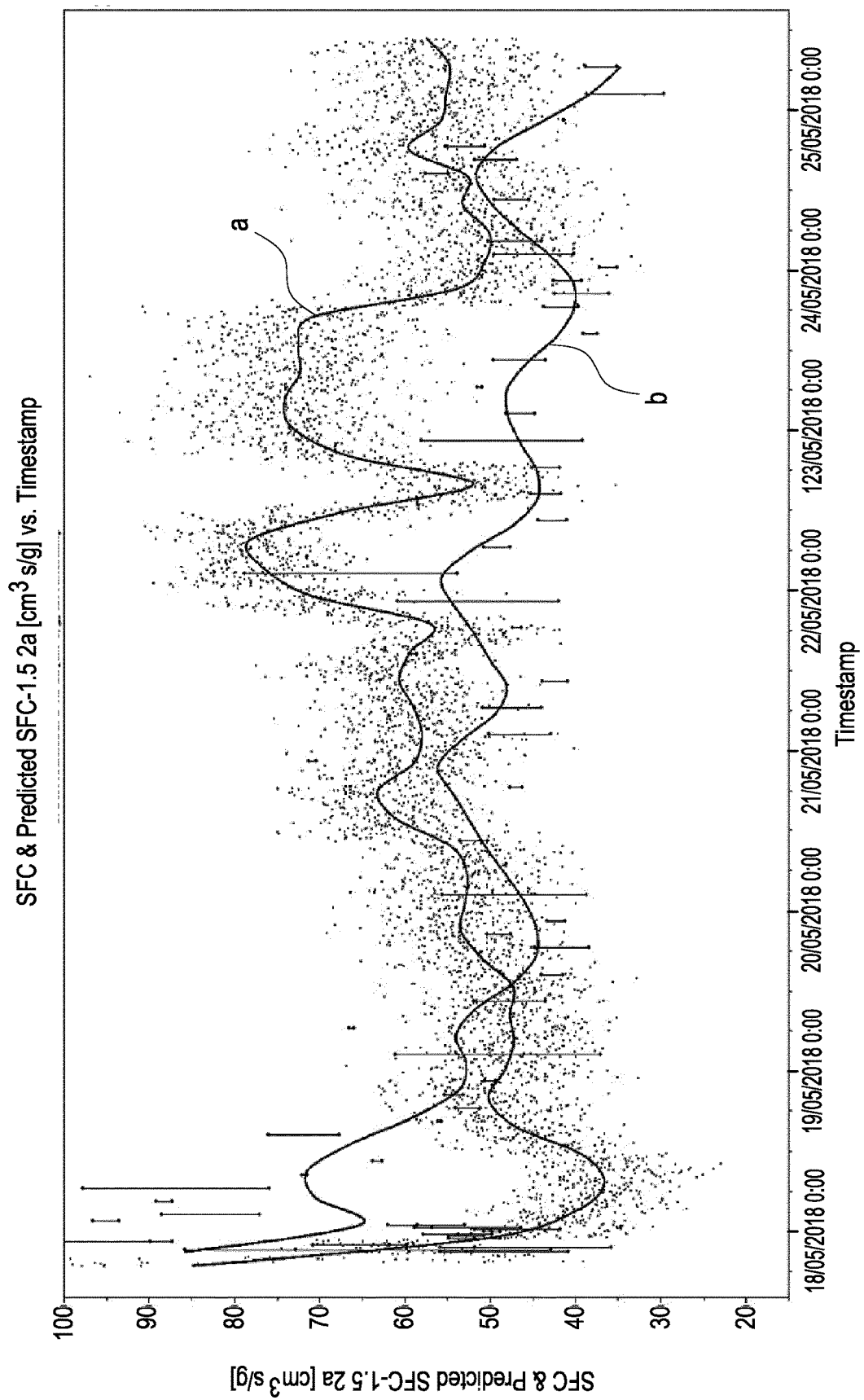
FIG. 2 shows predicted inline data vs. measured data of SFC for a superabsorbent polymer.

FIG. 2 shows predicted in-line data and the smoothed curve (a) calculated from the individual data points vs. measured data and the smoothed curve (b) calculated from the individual data points of the saline flow conductivity (SFC) for a superabsorbent polymer. Measured data are shown with error bars, predicted data without error bars. The data were collected over a period of one week. Raman spectra were measured in-line, with each spectrum recorded as 6 accumulations of 20 sec each, thus 2 minutes in total per spectrum.

Figure 3:
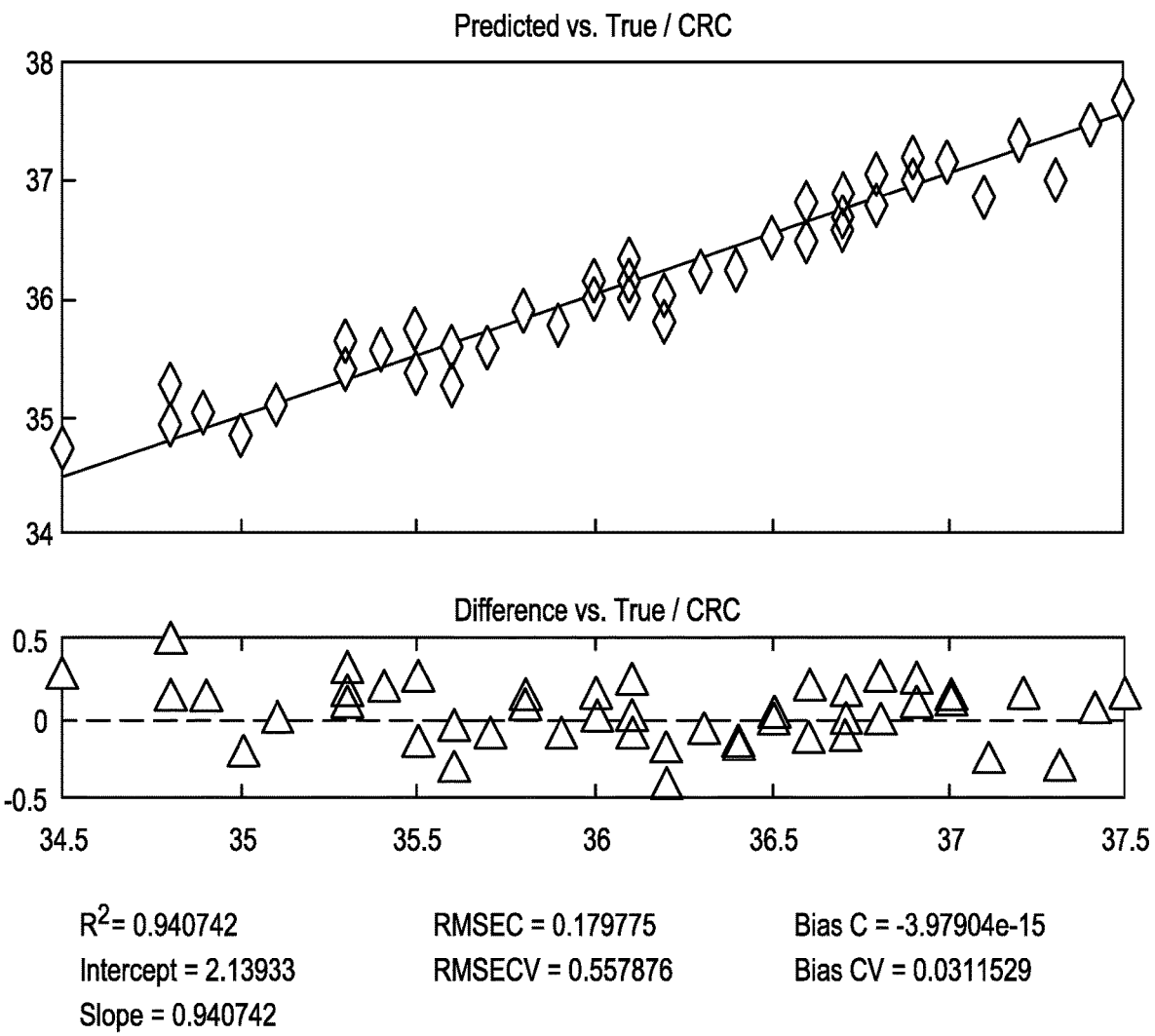
FIG. 3 shows the correlation of predicted vs. measured CRC for a range of superabsorbent polymers.

FIG. 3 shows the correlation of predicted vs. measured CRC for a range of superabsorbent polymers. A total number of 169 samples were included in the evaluation. A range of from 34 to 38 g/g was modeled. As is evident from the diagram and the indicated parameters, the predicted values closely match the values measured experimentally.

Figure 4:
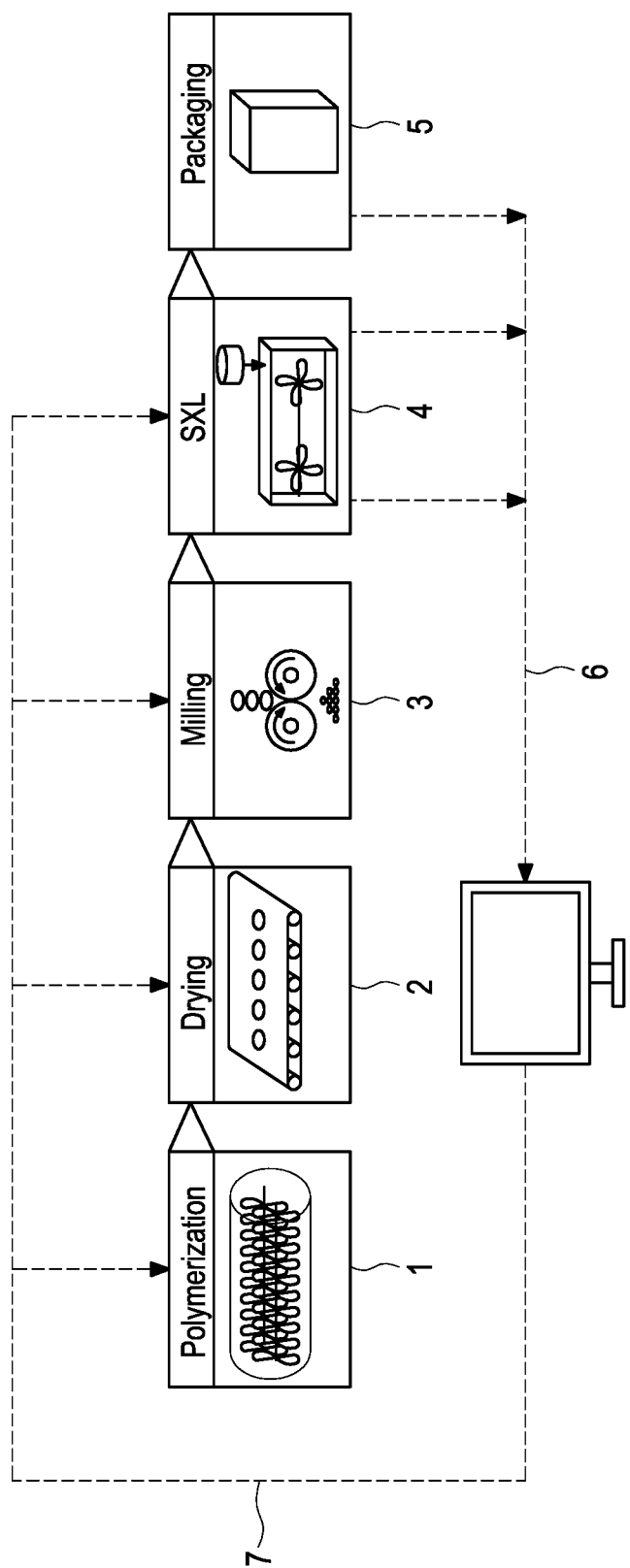
FIG. 4 is a schematic diagram of a production process of a superabsorbent polymer.

FIG. 4 is a schematic representation of a production process of a superabsorbent polymer. The production process includes the steps of (1) polymerization, (2) drying of the polymer, (3) milling of the polymer, (4) surface post-crosslinking (SXL) of the polymer; and finally, (5) packaging of the finished product. Predicted values of physical properties, e.g., performance parameters, of the superabsorbent polymer which have been obtained by the method of the present disclosure from spectroscopical data (6) collected by in-line Raman probes during process steps SXL and packaging, can be used in any of the process steps for steering (7) the process, i.e., controlling and optimizing process parameters.

Figure 5:
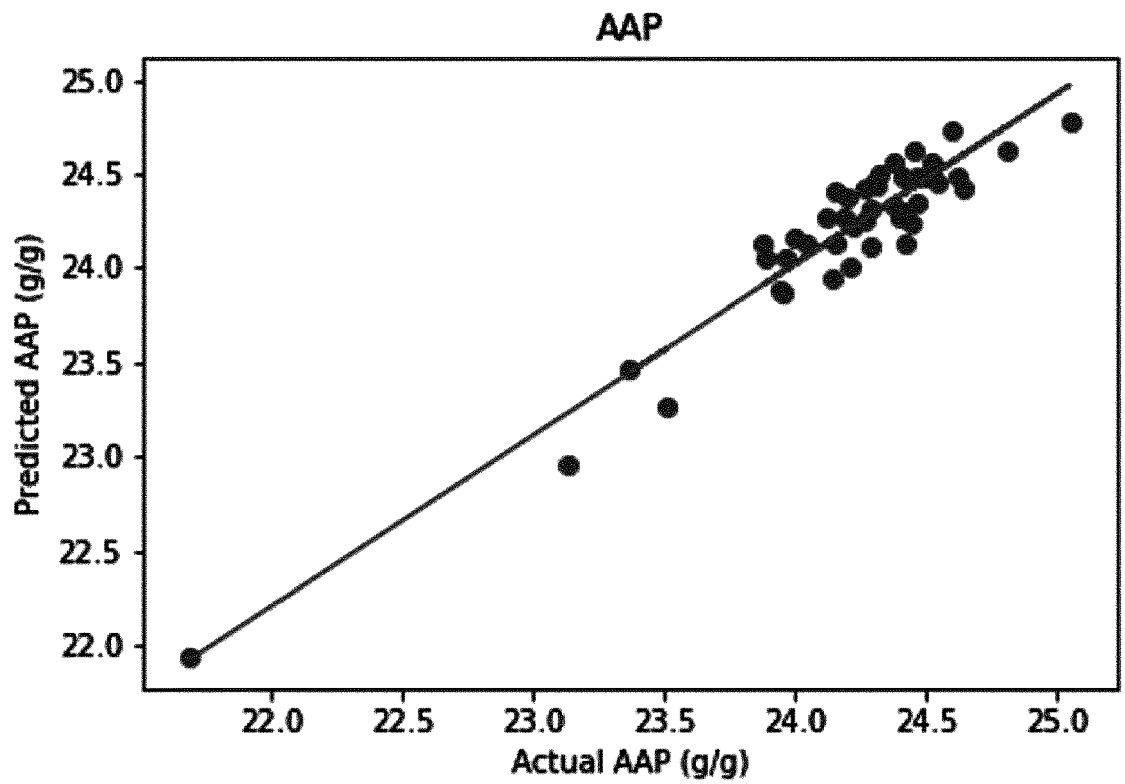
FIG. 5 shows the correlation of predicted vs. measured absorption against pressure (AAP) for a range of superabsorbent polymers.

FIG. 5 shows the predicted in-line data vs. the actual measured data measured offline in the lab for absorption against pressure (AAP) for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 21.5 to 25.2 g/g was modeled.

Figure 6:
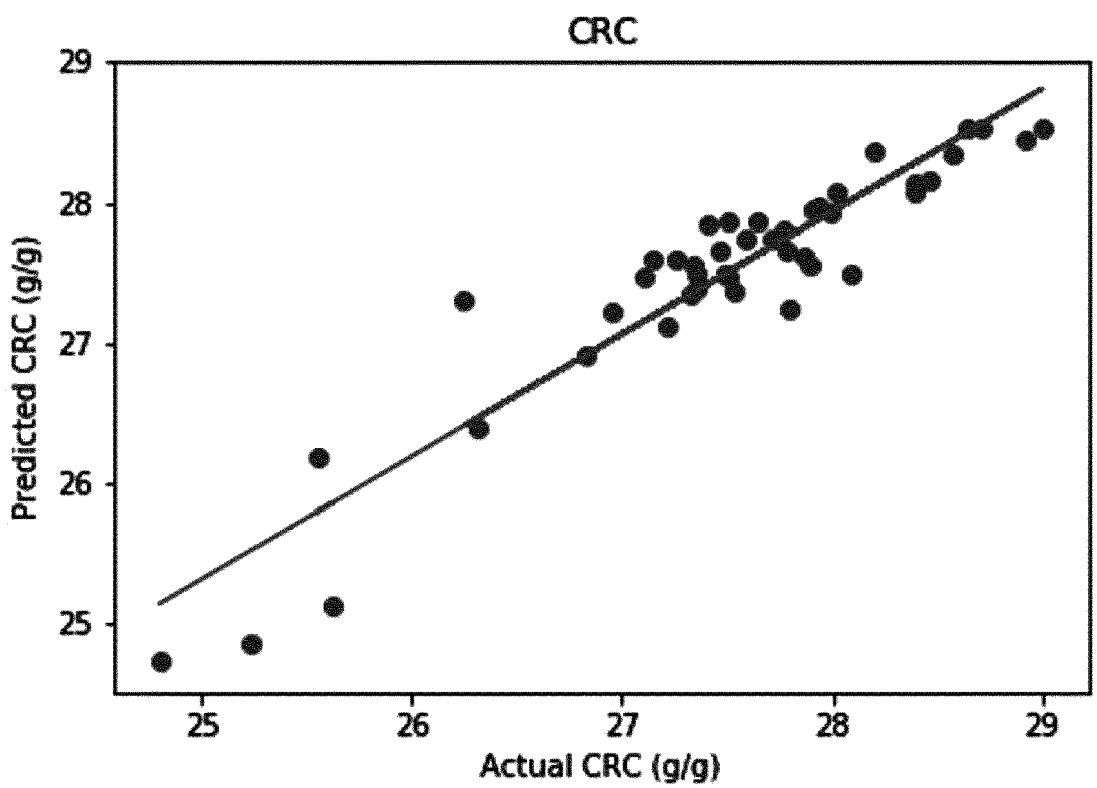
FIG. 6 shows the correlation of predicted vs. measured centrifugal retention capacity (CRC) for a range of superabsorbent polymers.

FIG. 6 shows the predicted in-line data vs. the actual measured data measured offline in the lab for centrifugal retention capacity (CRC) for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 24.5 to 29 g/g was modeled over 44 samples.

Figure 7:
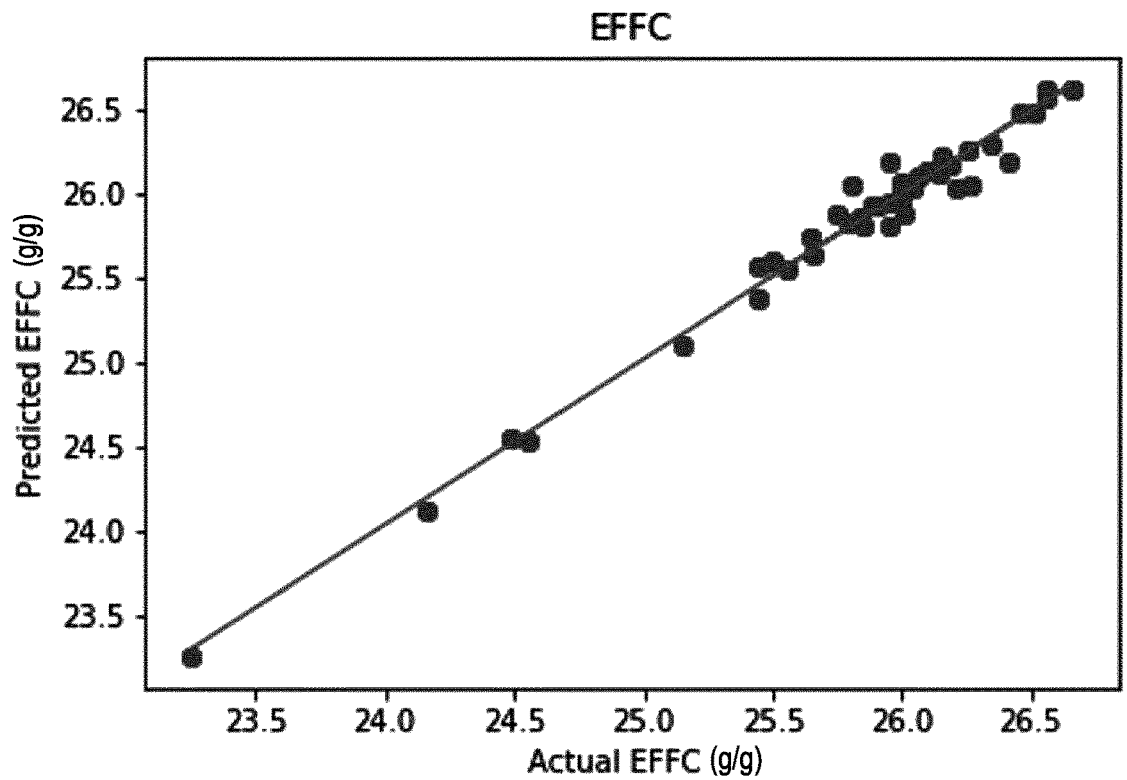
FIG. 7 shows the correlation of predicted vs. measured effective capacity (EFFC) for a range of superabsorbent polymers.

FIG. 7 shows the predicted in-line data vs. the actual measured data measured offline in the lab for effective capacity (EFFC) for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 24.5 to 29 g/g was modeled over 44 samples.

Figure 8:
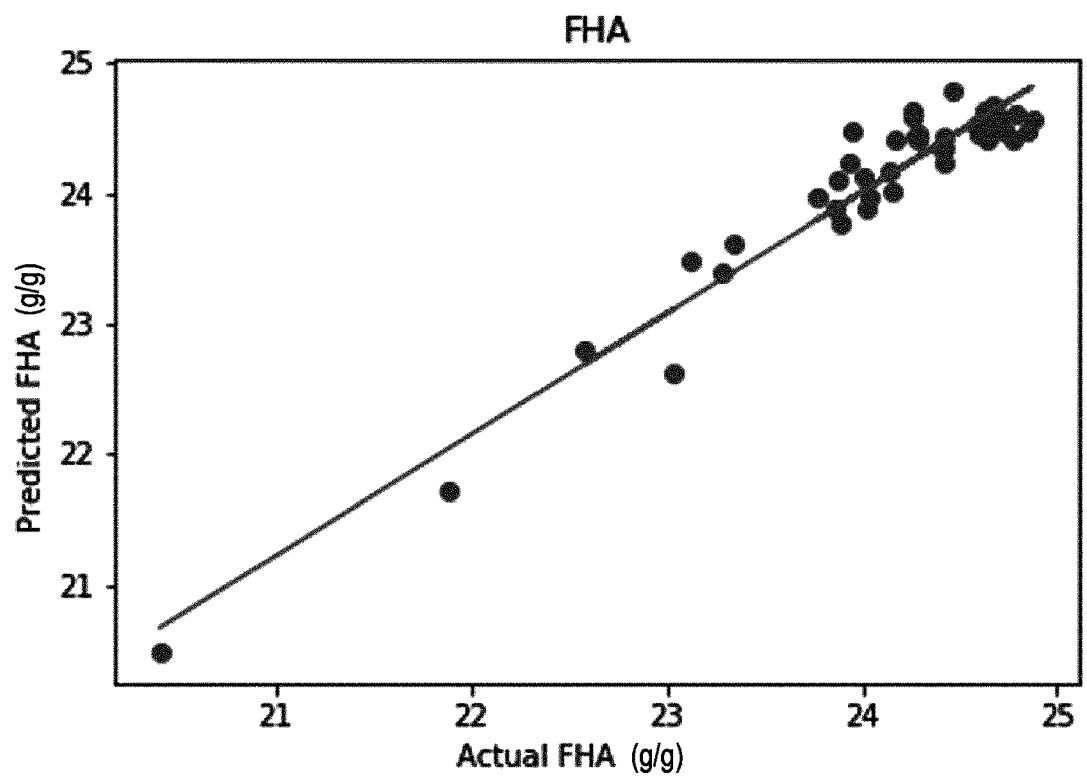
FIG. 8 shows the correlation of predicted vs. measured fixed height absorption (FHA) for a range of superabsorbent polymers.

FIG. 8 shows the predicted in-line data vs. the actual measured data measured offline in the lab for fixed height absorption (FHA) at a height of 20 cm for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 20.5 to 25 g/g was modeled over 44 samples.

Figure 9:
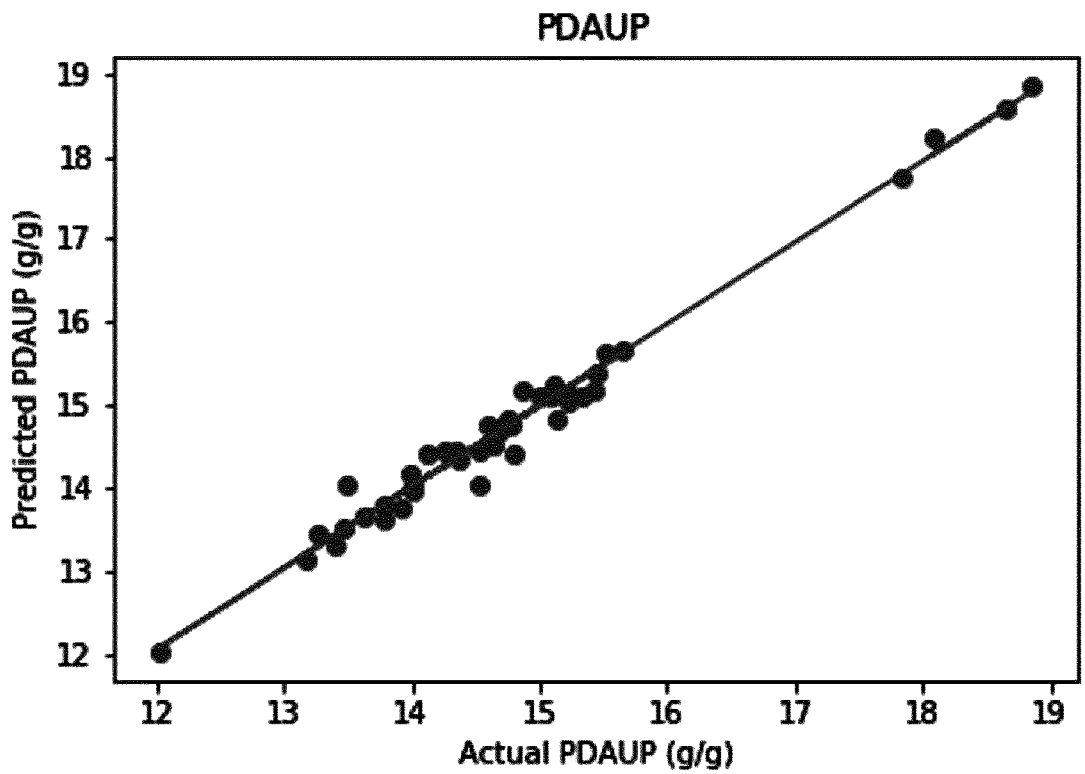
FIG. 9 shows the correlation of predicted vs. measured permeability dependent absorption under pressure (PDAUP) for a range of superabsorbent polymers.

FIG. 9 shows the predicted in-line data vs. the actual measured data measured offline in the lab for permeability dependent absorption under pressure (PDAUP) for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 12 to 19 g/g was modeled over 44 samples.

Figure 10:
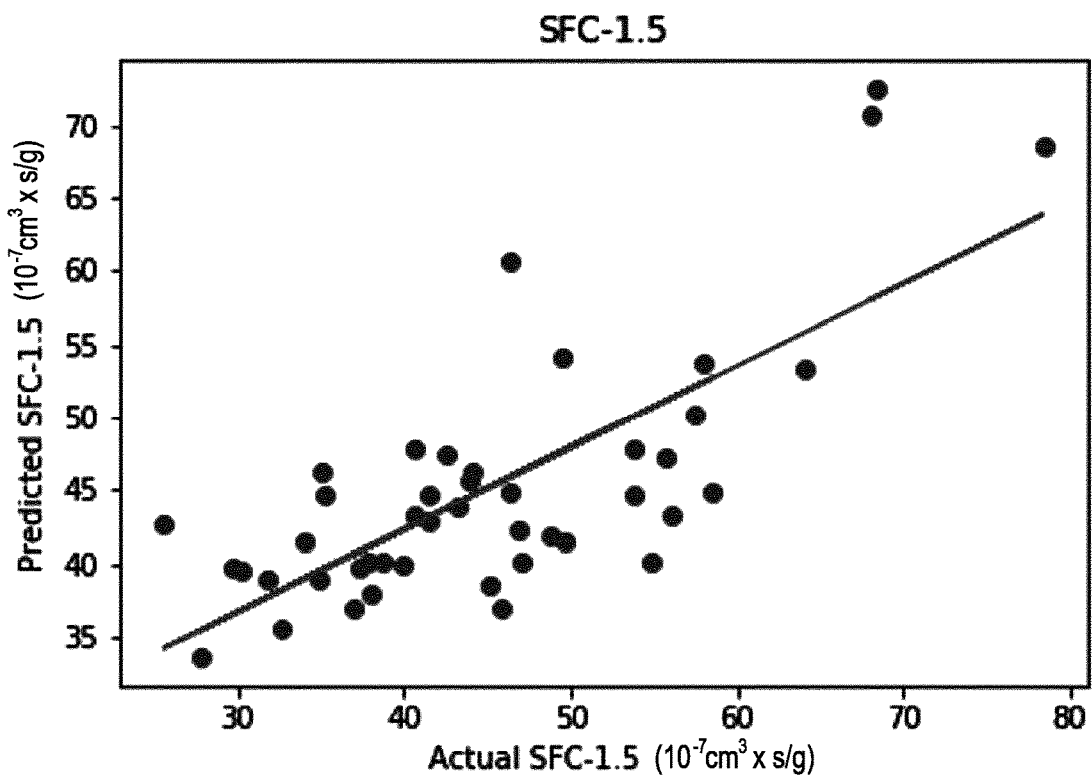
FIG. 10 shows the correlation of predicted vs. measured saline flow conductivity (SFC-1.5) for a range of superabsorbent polymers.

FIG. 10 shows the predicted in-line data vs. the actual measured data measured offline in the lab for saline flow conductivity (SFC-1.5) for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 25.5 to $80 \cdot 10^{-7}$ $cm^3 \cdot s/g$ was modeled over 44 samples.

Figure 11:
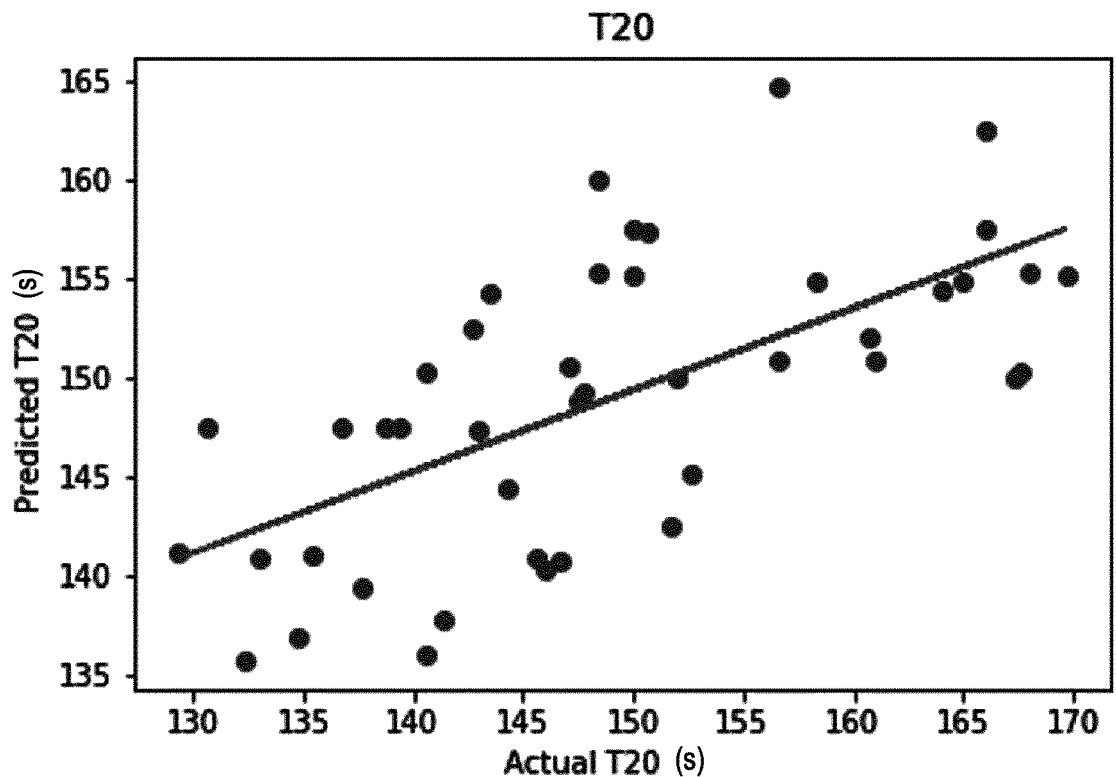
FIG. 11 shows the correlation of predicted vs. measured absorption time under pressure (T20) for a range of superabsorbent polymers.

FIG. 11 shows the predicted in-line data vs. the actual measured data measured offline in the lab for absorption time under pressure (T20) for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 128 to 175 s was modeled over 43 samples.

Figure 12:
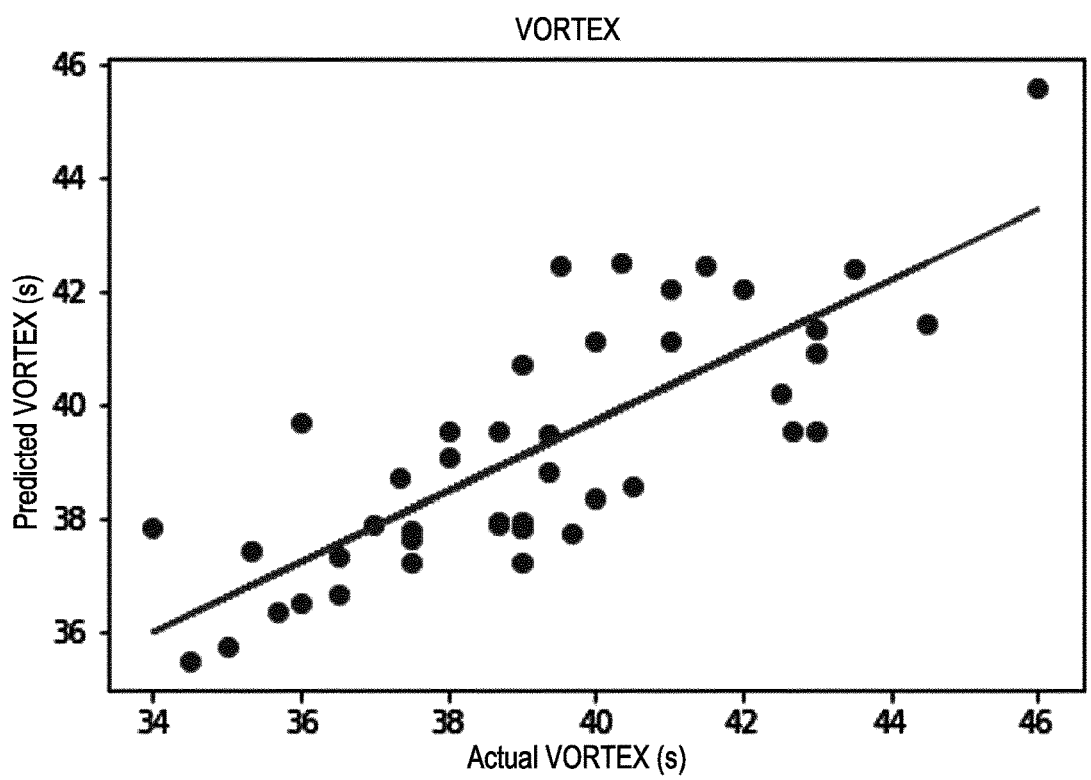
FIG. 12 shows the correlation of predicted vs. measured absorption time (VORTEX) for a range of superabsorbent polymers.

FIG. 12 shows the predicted in-line data vs. the actual measured data measured offline in the lab for absorption time (VORTEX) for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 34 to 46 s was modeled over 43 samples.

Figure 13:
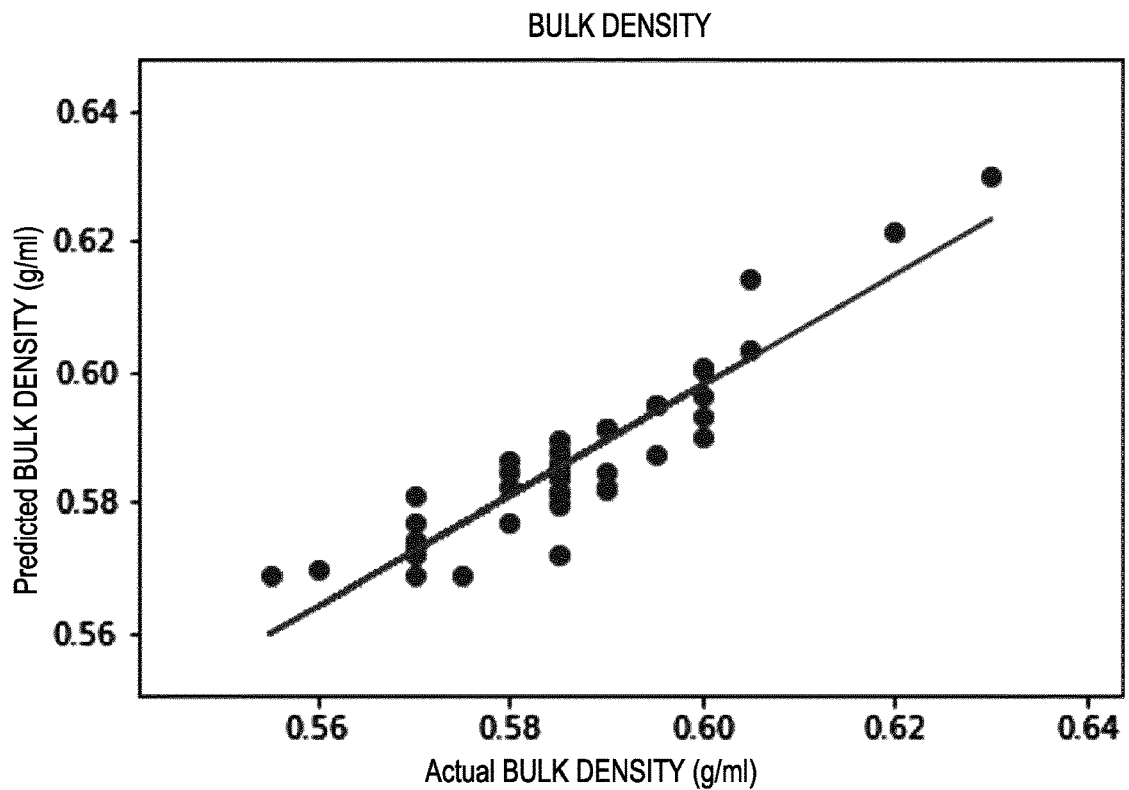
FIG. 13 shows the correlation of predicted vs. measured bulk density for a range of superabsorbent polymers.

FIG. 13 shows the predicted in-line data vs. the actual measured data measured offline in the lab for bulk density for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 0.55 to 0.63 g/ml was modeled over 44 samples.

Figure 14:
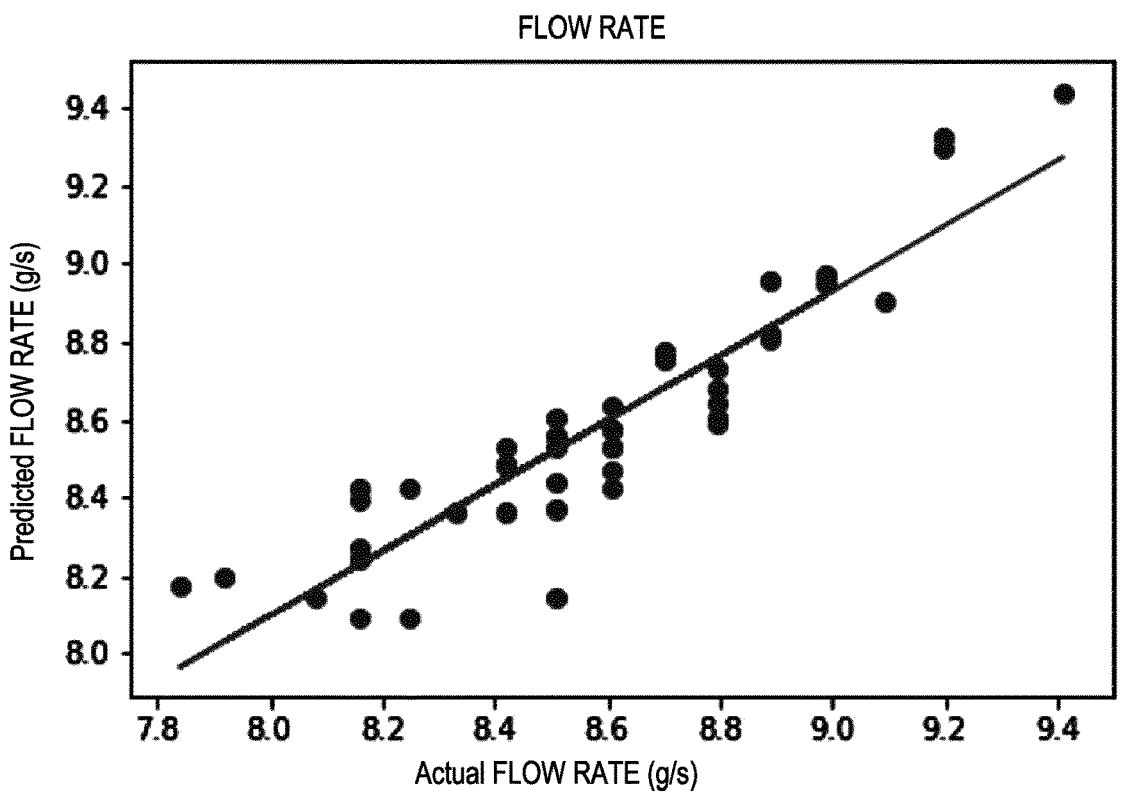
FIG. 14 shows the correlation of predicted vs. measured flow rate for a range of superabsorbent polymers.

FIG. 14 shows the predicted in-line data vs. the actual measured data measured offline in the lab for flow rate for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 7.8 to 9.4 g/s was modeled over 44 samples.

Figure 15:
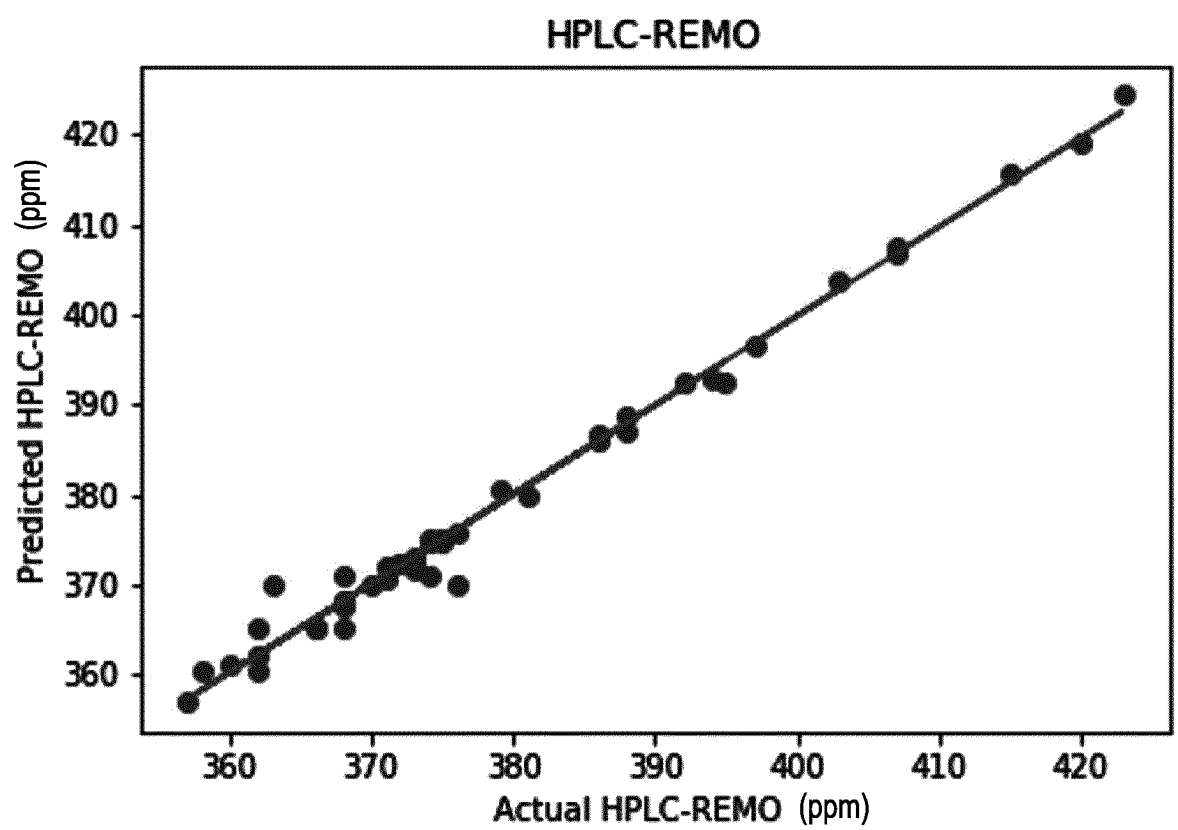
FIG. 15 shows the correlation of predicted vs. measured residual monomer content (ReMo) for a range of superabsorbent polymers.

FIG. 15 shows the predicted in-line data vs. the actual measured data measured by HPLC offline in the lab for residual monomer content (ReMo) for a range of superabsorbent polymers. The line depicts the correlation function between predicted and measured data. As is evident from the diagram, the predicted values closely match the values measured experimentally. Raman spectra were measured in-line, with each spectrum recorded as 6 accumulations of 20 sec each, thus 2 minutes in total per spectrum. A range of 350 to 430 ppm was modelled over 44 samples.

The invention claimed is:

1. A method of predicting at least one physical property of a superabsorbent polymer, comprising collecting a Raman spectrum of the superabsorbent polymer and using the Raman spectrum as input for a model which determines a value of the at least one physical property from spectroscopic data, wherein the model is based on a regression algorithm, wherein the at least one physical property includes a performance parameter of the superabsorbent polymer, a particle size distribution (PSD) of the superabsorbent polymer, or a bulk density of the superabsorbent polymer, wherein the Raman spectrum of the superabsorbent polymer is collected in-line in a production process of the superabsorbent polymer, and wherein the production process comprises the steps of polymerization, drying the polymer, milling the polymer, surface post-crosslinking of the polymer and packaging of a finished product.

2. The method of claim 1, wherein the model has been trained with Raman spectra and measured values of the at least one physical property of a plurality of superabsorbent polymers covering an extended range of values of the at least one physical property.

3. The method of claim 2, wherein a plurality of Raman spectra has been collected for each superabsorbent polymer and the spectroscopic data have been pre-treated by baseline correction of each Raman spectrum, optional smoothing or generation of a derivative of each Raman spectrum, and subsequent normalization of the Raman spectra.

4. The method of claim 1, wherein the Raman spectrum of the superabsorbent polymer is collected during the process steps surface post-crosslinking and/or packaging.

5. The method of claim 1, wherein the at least one physical property comprises at least one of the following performance parameters: centrifuge retention capacity (CRC), absorption against pressure (AAP), fixed height absorption (FHA), effective capacity (EFFC), saline flow conductivity (SFC or SFC 1.5 (UPM)), time in which the superabsorbent polymer reaches a liquid uptake of 20 g/g (T20), or Vortex.

6. The method of claim 1, wherein the at least one physical property comprises particle size distribution (PSD) or bulk density of the superabsorbent polymer.

7. The method of claim 1, wherein the superabsorbent polymer comprises cross-linked polymer chains of at least partially neutralized acrylic acid monomer units.

8. The method of claim 1, further comprising controlling production of a superabsorbent polymer by varying a concentration of crosslinker in the polymerization step or by varying a concentration of surface-crosslinker or by optimization of process steering parameters comprising use of the determined value for the at least one physical property.

9. A non-transitory computer program product that, when loaded into a memory of a computing device, and executed by at least one processor unit of the computing device, executes the steps of the method according to claim 1.

10. A computer system for predicting at least one physical property of a superabsorbent polymer, the computer system comprising at least:
an interface component configured to access and read a Raman spectrum of the superabsorbent polymer; and
a processor unit implementing a model and configured to use the Raman spectrum provided via the interface component as input for the model which determines a value of the at least one physical property from spectroscopic data, wherein the model is on a regression algorithm;
wherein the at least one physical property includes a performance parameter of the superabsorbent polymer, a particle size distribution (PSD) of the superabsorbent polymer, or a bulk density of the superabsorbent polymer; and
wherein the Raman spectrum of the superabsorbent polymer was collected in-line in a production process of the superabsorbent polymer, and wherein the production process comprises the steps of polymerization, drying the polymer, milling the polymer, surface post-crosslinking of the polymer and packaging of a finished product.

11. The system according to claim 10, which is configured to be coupled to a Raman spectrometer via a wired and/or wireless communication connection, and to access and read out the Raman spectrum at least partly automatically from the Raman spectrometer via the interface component.

12. The system according to claim 10, which is configured to determine the value of the at least one physical property from the spectroscopic data in-line in a production process of the superabsorbent polymer.

13. The system according to claim 10, which further comprises a database which at least temporarily stores a plurality of measured Raman spectra and measured values of the at least one physical property of a plurality of superabsorbent polymers covering an extended range of values of the at least one physical property, the system being further configured to train the model with the stored measured Raman spectra and the measured values of the at least one physical property.

14. The system according to claim 13, which is configured to continuously update the model over and over again by iteratively training the model with newly measured Raman spectra and newly measured values of the at least one physical property of superabsorbent polymers.

* * * * *